United States Patent [19]
Hu

[11] Patent Number: 5,541,970
[45] Date of Patent: Jul. 30, 1996

[54] IMAGE RECONSTRUCTION FOR A CT SYSTEM IMPLEMENTING A FOUR FAN BEAM HELICAL SCAN

[75] Inventor: Hui Hu, Waukesha, Wis.

[73] Assignee: General Electric Company, Milwaukee, Wis.

[21] Appl. No.: 436,176

[22] Filed: May 9, 1995

[51] Int. Cl.⁶ .................................................. G01N 23/00
[52] U.S. Cl. .......................... 378/4; 364/413.17; 378/901
[58] Field of Search .................... 378/4, 901; 364/413.17

[56] References Cited

U.S. PATENT DOCUMENTS

| | | |
|---|---|---|
| 4,580,219 | 4/1989 | Pelc et al. . |
| 4,821,210 | 4/1989 | Rumbaugh . |
| 5,047,931 | 9/1991 | Lin . |
| 5,233,518 | 8/1993 | King et al. . |
| 5,253,171 | 10/1993 | Hsiao et al. . |
| 5,265,142 | 11/1993 | Hsieh . |
| 5,270,923 | 12/1993 | King et al. . |

OTHER PUBLICATIONS

Crawford et al., Computed Tomography Scanning with Simultaneous Patient Translation, Med. Phys. 17(6), Nov./Dec. 1990, pp. 967–982.

*Primary Examiner*—Craig E. Church
*Attorney, Agent, or Firm*—John S. Beulick; John H. Pilarski

[57] ABSTRACT

The present invention, in one form, is an apparatus for performing image reconstruction using data obtained by a four beam helical scan. In reconstructing an image, projection data arrays are generated. Such projection data is then weighted by weighting factors to generate a weighted projection data array. The weighted projection data array is filtered and back projected to generate an image data array. The image data arrays for the beams are then summed to generate a slice image data array.

15 Claims, 6 Drawing Sheets

IMAGE RECONSTRUCTION FOR A CT SYSTEM IMPLEMENTING A FOUR FAN BEAM HELICAL SCAN

FIELD OF THE INVENTION

This invention relates generally to computed tomography (CT) imaging and more particularly, to tile reconstruction of images from data acquired from a helical scan using four the beams.

BACKGROUND OF THE INVENTION

In CT systems, an x-ray source projects a fan-shaped beam which is collimated to lie within an X-Y plane of a Cartesian coordinate system, termed the "imaging plane". The x-ray beam passes through tile object being imaged, such as a patient, and impinges upon a linear array of radiation detectors. The intensity of the transmitted radiation is dependent upon the attenuation of the x-ray beam by the object. Each detector of the linear array produces a separate electrical signal that is a measurement of the beam attenuation. The attenuation measurements from all the detectors are acquired separately to produce a transmission profile.

The x-ray source and the linear detector array in a CT system are rotated with a gantry within the imaging plane and around the object so that the angle at which the x-ray beam intersects the object constantly changes. A group of x-ray attenuation measurements from the detector array at one gantry angle is referred to as a "view". A "scan" of the object comprises a set of views made at different gantry angles during one revolution of the x-ray source and detector. In an axial scan, data is processed to construct an image that corresponds to a two dimensional slice taken through the object. One method for reconstructing an image from a set of data is referred to in the art as the filtered back projection technique. This process converts the attenuation measurements from a scan into integers called "CT numbers" or "Hounsfield units", which are used to control the brightness of a corresponding pixel on a cathode ray tube display.

To reduce the total scan time required for multiple slices, a "helical" scan may be performed. To perform a "helical" scan, the patient is moved while the data for the prescribed number of slices is acquired. A four beam helical scan may be used to even further reduce the total scan time. Such a scan is made by utilizing a CT system in which four rows of detectors simultaneously collect projection measurements at different axial locations. The four detector rows define four fan beams. Such a system generates interwoven quadruple helixes, as opposed to a single helix from a conventional one fan beam helical scan. The interwoven helixes mapped out by the four fan beams yield projection data from which images in each prescribed slice may be reconstructed.

It is desirable, of course, to reconstruct images from the data obtained in a four beam helical scan in a manner which provides a high quality image with a minimum level of artifacts. It also is desirable to reduce the total time required to reconstruct such an image.

SUMMARY OF THE INVENTION

The present invention, in one form, includes apparatus for performing image reconstruction using data obtained by a four beam helical scan. More particularly, in accordance with the one form of the present invention, projection space data arrays are selected from projection data acquired by each fan beam. Data in each array is then weighted to correct for the translational motion of the patient and to offset data redundancy effects. An image is then reconstructed using the weighted data.

More specifically, in reconstructing an image, projection data arrays are generated. The projection data arrays correspond to data planes associated with the slice to be imaged. Weighting factors are then applied to the data arrays to assign a weight to each particular data element. The weighted projection data arrays are then filtered and back projected to generate an image data array. The image data arrays are then summed to generate a slice image data array.

Using a four beam helical scan of a patient provides the advantage that total patient scan time is reduced. Further, the image reconstruction algorithm described above provides that advantage that even though the patient table translation speed is increased, a high quality image slice may be generated.

DETAILED DESCRIPTION OF THE DRAWINGS

Figure 1:
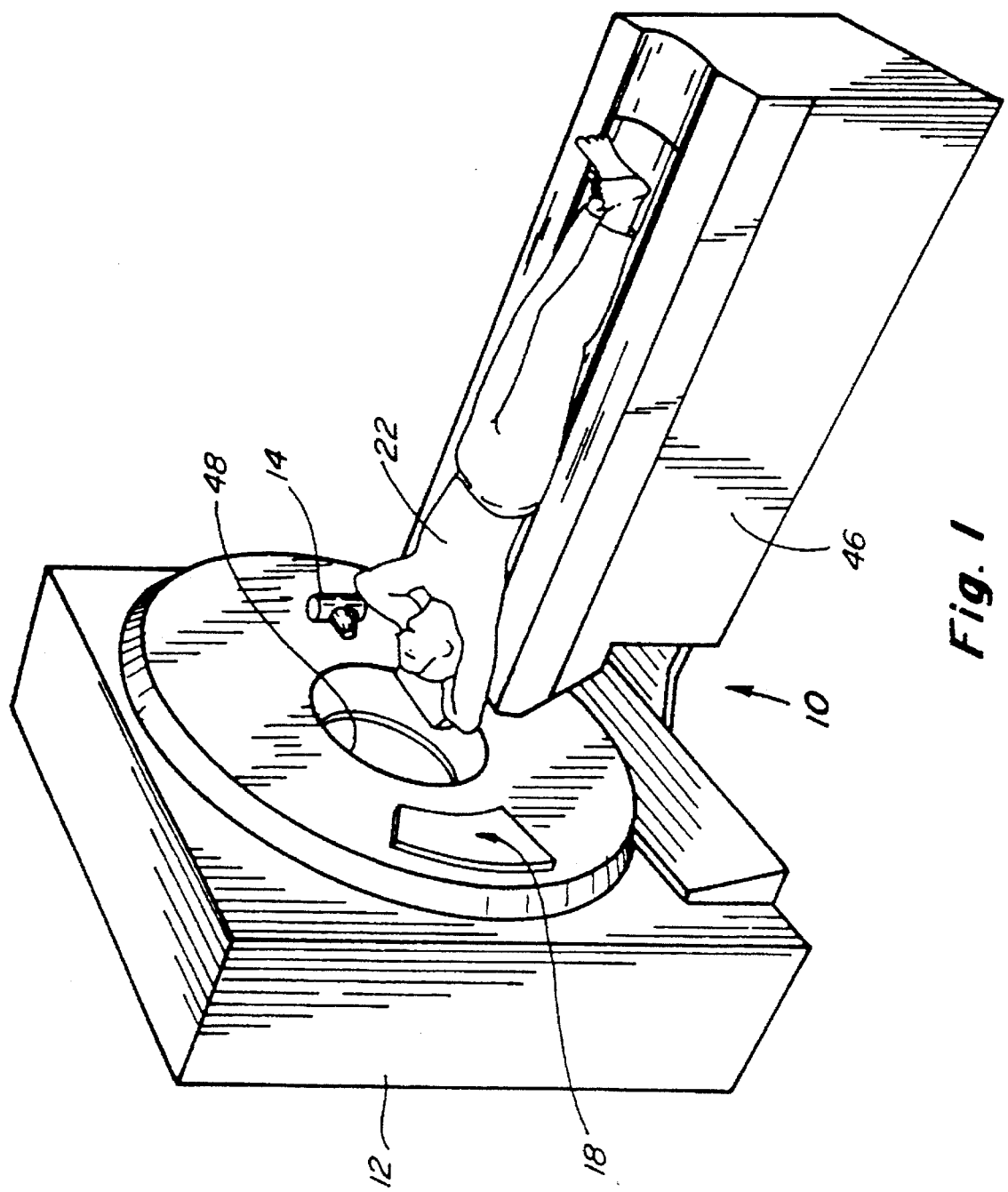
FIG. 1 is a pictorial view of a CT imaging system.
Figure 2:
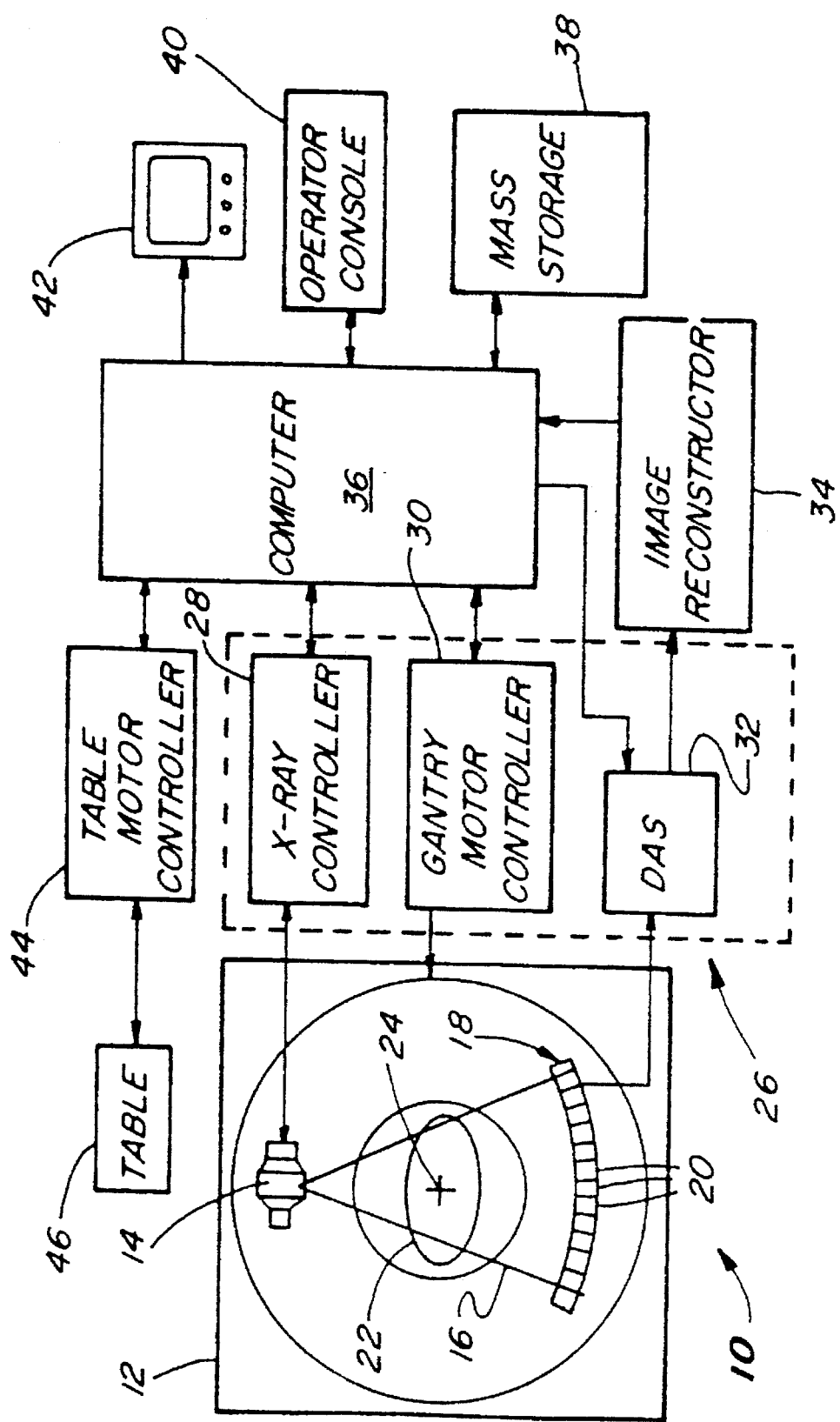
FIG. 2 is a block schematic diagram of the system illustrated in FIG. 1.

With reference to FIGS. 1 and 2, a computed tomography (CT) imaging system 10 includes a gantry, 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through a medical patient 22. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scamping parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

Figure 3:
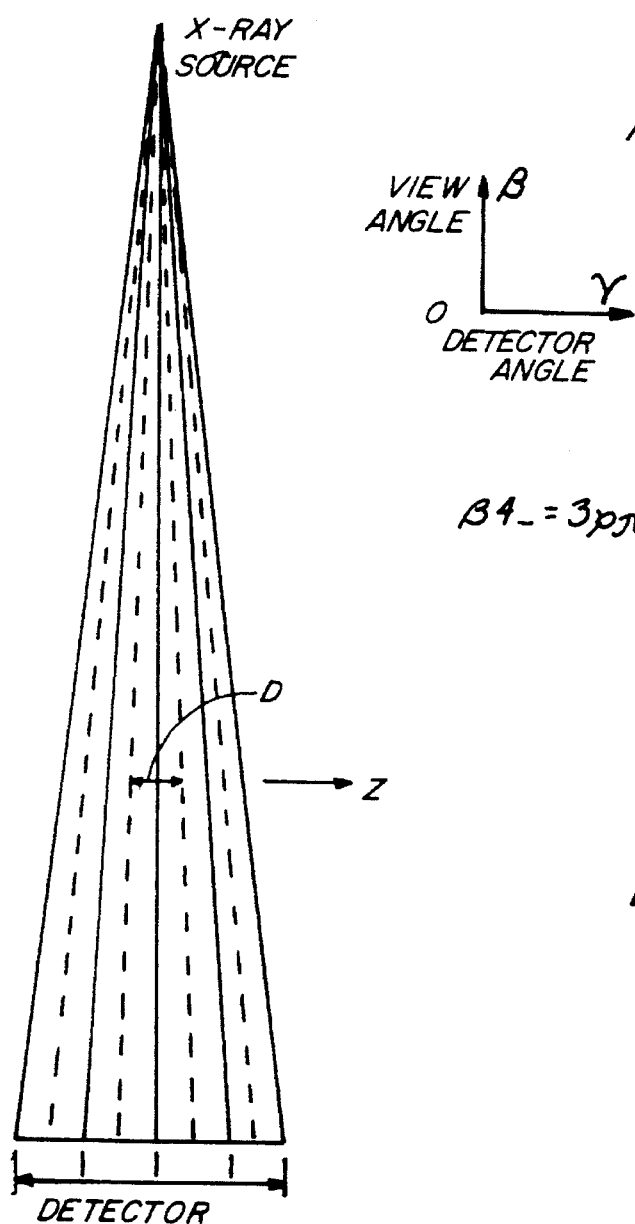
FIG. 3 is a schematic representation of a four beam X-ray in cross section along the z-axis.

As shown in FIG. 3, four rows of detectors are defined in a four fan beam system. The x-ray fan beam is, in effect, split into four fan beams displaced along the z-axis of rotation. The distance between the center of adjacent beams is D when measured at the axis of gantry rotation.

Figure 4:
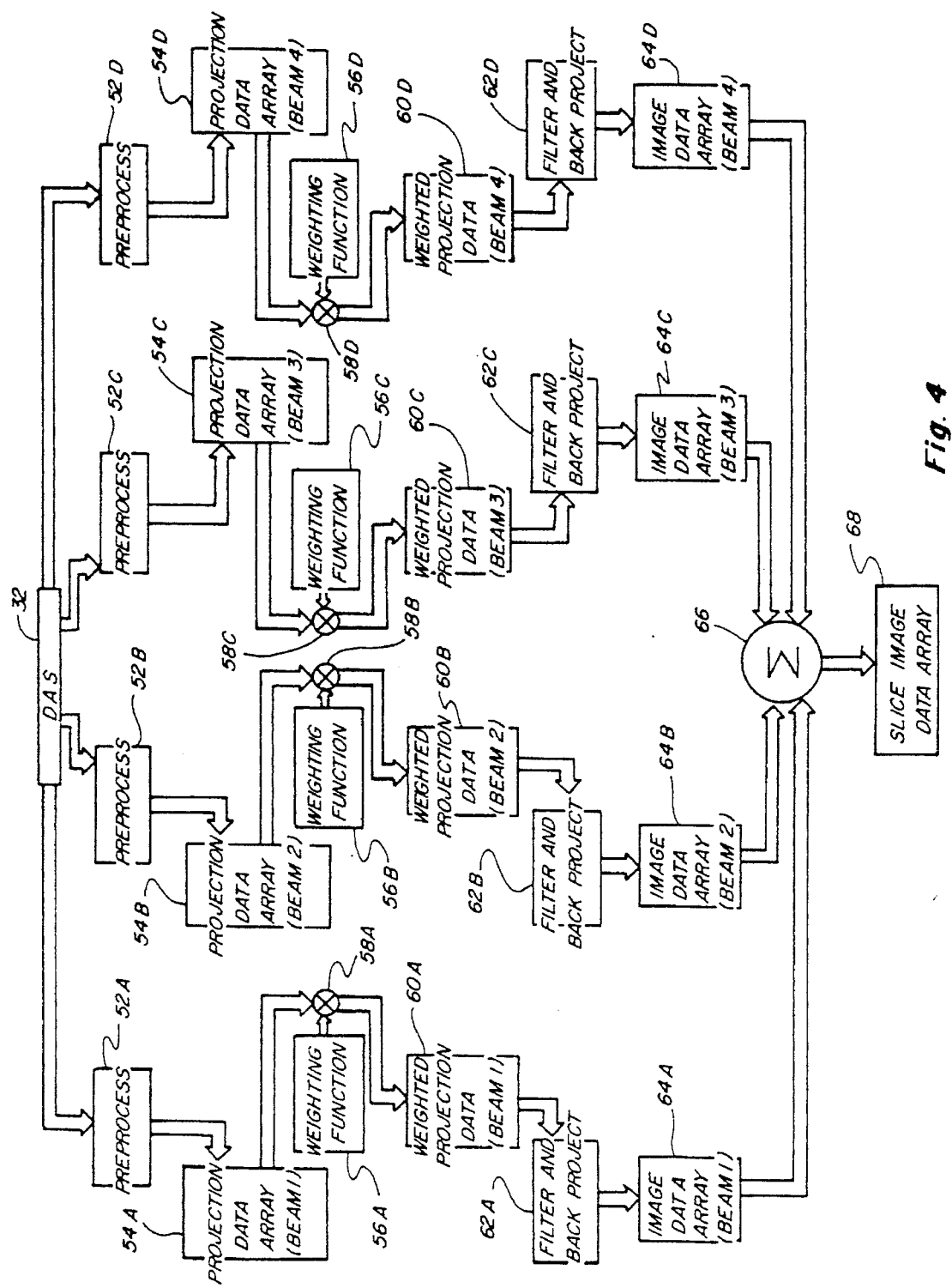
FIG. 4 is a block diagram of an image reconstructor which forms part of the CT imaging system of FIG. 2.

Image reconstructor 34 is shown in more detail in FIG. 4. Particularly, each view of data from DAS 32 for each fan beam is received at respective preprocessors 52A–D where the respective beam is preprocessed to correct for various well-known errors such as beam hardening, offsets and variations in detector and channel gain. Also, the negative logarithm is taken to provide projection data which is stored in a projection data array 54A–D.

The projection data for each beam array 54A–D is read out and a corresponding weighting function 56A–D is applied at multipliers 58A–D. The weighted projection data is written into a corresponding location in weighted projection data array 60A–D, and this weighted projection data is filtered and back projected 62A–D to produce a beam image data array 64A–D.

Image data arrays 64A–D are then summed 66 to generate a slice image data array 68. Specifically, the magnitude of each pixel in beam 1 array is summed with the magnitude of the corresponding pixels in the beam 2, beam 3 and beam 4 arrays. The resulting slice image array 68 may be stored for later use or displayed to the operator. Rather than summing the data subsequent to generation of image data arrays 64A–D, the projections from the same gantry (view) angle but from different detector rows can be combined prior to filtering and back projecting the data. Such a combination reduces the processing load.

The present invention, in one form, relates specifically to the creation of weighted projection data arrays 60A–D when the four beam scan has been performed under certain predetermined conditions. With respect to the following discussion, d denotes the detector row (the z) spacing measured at the axis of the gantry rotation, s denotes the table feeding speed (per rotation), and p denotes the ratio of d and s, that is:

$$p = d/s. \quad (1)$$

Figure 5:
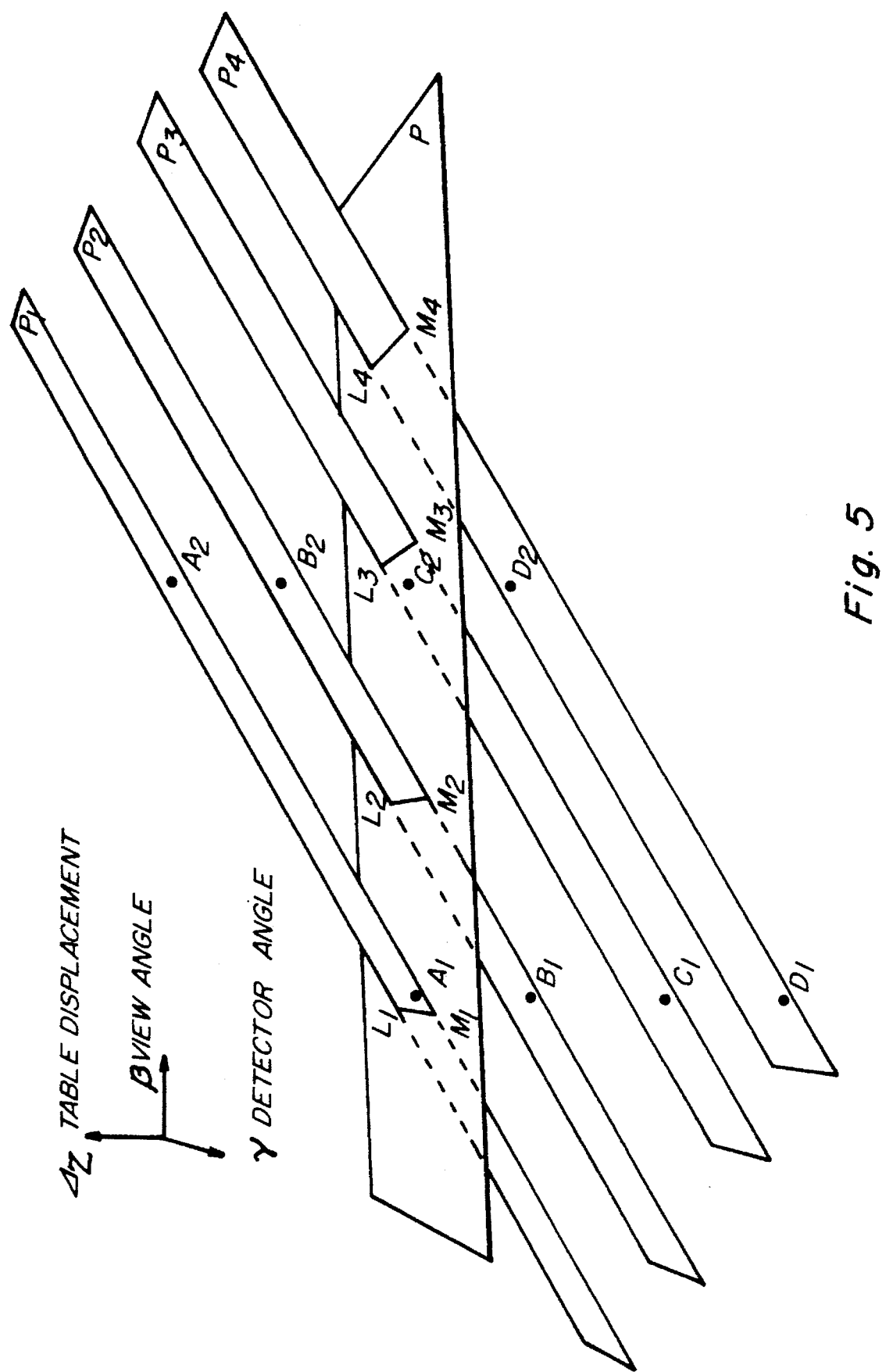
FIG. 5 illustrates the intersection of four data planes with an image slice.

As shown in FIG. 5, data planes $P_1$, $P_2$, $P_3$ and $P_4$ intercept slice P to be reconstructed at lines $L_1M_1$, $L_2M_2$, $L_3M_3$, and $L_4M_4$. These line functions can be expressed as:

$$\begin{aligned} L_1M_1: & \; \beta 1 = -3p\pi, \\ L_2M_2: & \; \beta 2 = -p\pi, \\ L_3M_3: & \; \beta 3 = p\pi, \\ L_4M_4: & \; \beta 4 = 3p\pi, \end{aligned} \quad (2)$$

where $\beta$ is equal to the gantry angle. Lines $L_1M_1$, $L_2M_2$, $L_3M_3$, and $L_4M_4$ have "mirror" lines, denoted as+and−sets as follows:

$$\begin{aligned} \beta 1_\pm &= -3p\pi \pm \pi - 2\gamma, \\ \beta 2_\pm &= -p\pi \pm \pi - 2\gamma, \\ \beta 3_\pm &= p\pi \pm \pi - 2\gamma, \\ \beta 4_\pm &= 3p\pi \pm \pi - 2\gamma, \end{aligned} \quad (3)$$

where $\gamma$ is equal to the detector angle.

When the table feeding speed s and the detector z spacing, d, satisfy the relation $(4\pi/(\pi-2\gamma_m))d < s < (6\pi/(\pi-2\gamma_m))d$, where $\gamma_m$ is defined as half of the fan angle, the helical weighting factor to be applied for each data set, denoted as $W1(\beta,\gamma)$, $W2(\beta,\gamma)$, $W3(\beta,\gamma)$ and $W4(\beta,\gamma)$ are:

$$W1(\beta,\gamma) = 1/2 \begin{cases} 0 & \beta \leq \beta 3_- \\ \dfrac{\beta - \beta 3}{\beta 1 - \beta 3_-} & \beta 3_- < \beta \leq \beta 1 \\ \dfrac{\beta - \beta 2}{\beta 1 - \beta 2} & \beta 1 < \beta < \beta 2_- \\ 0 & \beta \geq \beta 2 \end{cases} \quad (4)$$

$$W2(\beta,\gamma) = \begin{cases} 0 & \beta \leq \beta 3_- \\ w2_1(\beta,\gamma) + w2_2(\beta,\gamma) & \beta 3_- < \beta \leq \beta 2 \\ \dfrac{\beta - \beta 3}{\beta 2 - \beta 3} & \beta 2 < \beta < \beta 3 \\ 0 & \beta \geq \beta 3 \end{cases} \quad (5)$$

where:

$$w2_1(\beta,\gamma) = 1/2 \begin{cases} 0 & \beta \leq \beta 1 \\ \dfrac{\beta - \beta 1}{\beta 2 - \beta 1} & \beta 1 < \beta \leq \beta 2 \\ 0 & \beta \geq \beta 2 \end{cases}$$

$$w2_2(\beta,\gamma) = 1/2 \begin{cases} 0 & \beta \leq \beta 4_- \\ \dfrac{\beta - \beta 4_-}{\beta 2 - \beta 4_-} & \beta 4_- < \beta \leq \beta 2 \\ 0 & \beta > \beta 2 \end{cases}$$

$$W3(\beta,\gamma) = \begin{cases} 0 & \beta \leq \beta 2 \\ \dfrac{\beta - \beta 3}{\beta 2 - \beta 3} & \beta 2 < \beta < \beta 3 \\ w3_1(\beta,\gamma) + w3_2(\beta,\gamma) & \beta 3 \leq \beta < \beta 2_+ \\ 0 & \beta \geq \beta 2_+ \end{cases}$$

where:

$$w3_1(\beta,\gamma) = 1/2 \begin{cases} 0 & \beta < \beta 3 \\ \dfrac{\beta - \beta 1_+}{\beta 3 - \beta 1_+} & \beta 3 \leq \beta < \beta 1_+ \\ 0 & \beta \geq \beta 1_+ \end{cases} \quad (6)$$

$$w3_2(\beta,\gamma) = 1/2 \begin{cases} 0 & \beta < \beta 3 \\ \dfrac{\beta - \beta 4}{\beta 3 - \beta 4} & \beta 3 \leq \beta < \beta 4 \\ 0 & \beta \geq \beta 4 \end{cases}$$

$$W4(\beta,\gamma) = 1/2 \begin{cases} 0 & \beta \leq \beta 3 \\ \dfrac{\beta - \beta 3}{\beta 4 - \beta 3} & \beta 3 < \beta \leq \beta 4 \\ \dfrac{\beta - \beta 2_+}{\beta 4 - \beta 2_+} & \beta 4 < \beta < \beta 2_+ \\ 0 & \beta \geq \beta 2_+ \end{cases} \quad (7)$$

Figure 6:
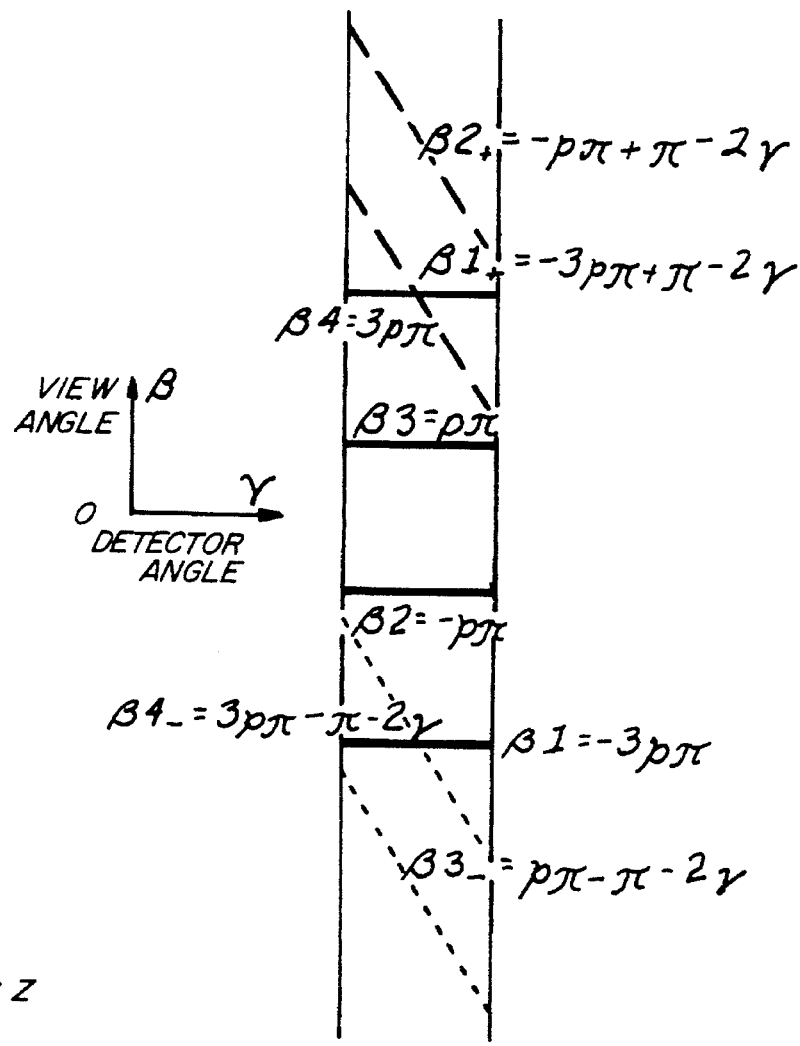
FIG. 6 illustrates a data plane and various data regions.
Figure 7:
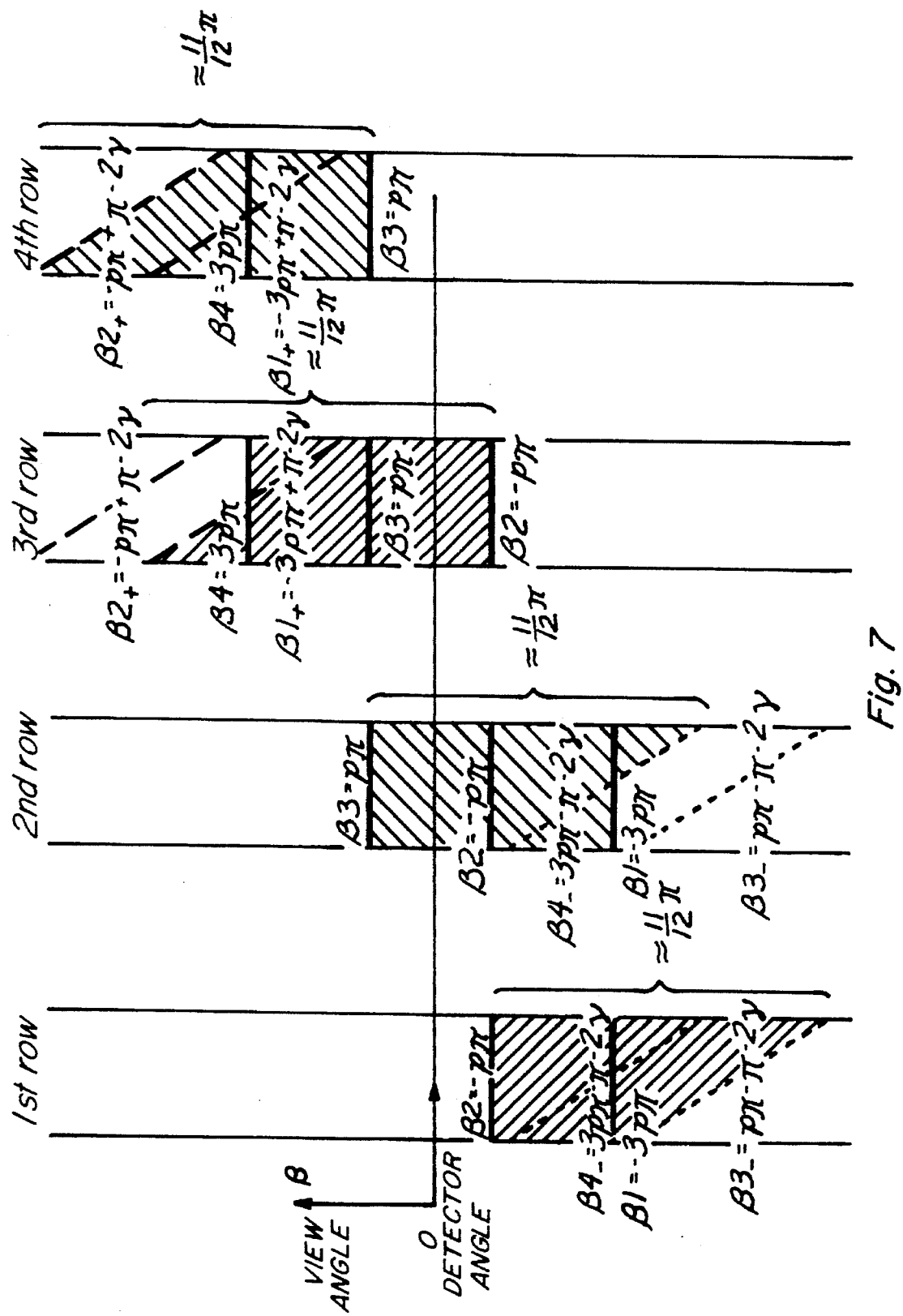
FIG. 7 illustrates four data planes and selected data regions utilized for constructing an image slice.

The regions in the data planes defined by the weighting function are illustrated in FIGS. 6 and 7. The shaded areas in FIG. 7 represent the data from each data plane used to reconstruct an image slice. For a fan angle $2\gamma_m = \pi/4$, the operable range for this image reconstruction algorithm is $16/3 \, d < s < 8d$.

The weighting functions described in Equations 4–7 are continuous. However, the first derivative for each such equation is discontinuous at the boundary lines. If necessary, this discontinuity can be eliminated by feathering a few channels (~10 channels) across the boundary.

Once weighted to create weighted projection data arrays 60A–D, and to reduce processing time, the projections from the same gantry (view) angle but from different detector rows can be combined prior to filtration and back projection. Some projection views in data row 1 are 360 degrees apart of the corresponding projection views in data row 4. These view pairs can be further combined prior to the filtration to eliminate any unnecessary increase in processing load.

With respect to the algorithm described above, roughly $3.67\pi$ worth of projection data needs to be preprocessed to reconstruct one slice. Compared to the amount of data needed to reconstruct an image in conventional scans (both axial and helical), the preprocessing load increases by 1.8 times in a four beam helical scan.

The projection data required for reconstructing adjacent slices can be identified by vertically shifting the origin of the view angle $\beta$ to align to a new slice to be reconstructed. In most cases, there are significant overlaps between the data for one slice and for the adjacent slices in each data set. Prior to weighting, the preprocessing is not slice-position-dependent. Thus, preprocessing (without helical weighting) results can be stored in buffers for future reuse. This greatly reduces the preprocessing load in most cases, especially in retrospective reconstruction.

If the desired slice profile is thicker than the profiles supported by the data and reconstruction algorithms described above, a thicker slice can be derived by summing multiple thin slices within the desired slice profile. If the multiple thin slices by themselves, are not of interest, the intermediate step of reconstructing multiple thin slices can be bypassed by performing the corresponding summation early in the projection domain. This reduces the computation load and the image storage load. The resultant weighting functions can be derived by summing corresponding shifted versions of the data planes.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. For example, the CT system described herein is a "third generation" system in which both the x-ray source and detector rotate with the gantry. Many other CT systems including "fourth generation" systems wherein the detector is a full-ring stationary detector and only the x-ray source rotates with the gantry, may be used. Accordingly, the spirit and scope of the invention are to be limited only by the terms of the appended claims.

What is claimed is:

1. A system for producing a tomographic image of an object from projection data acquired in a helical scan, said system generating data from four x-ray fan beams, said tomographic image system comprising an image reconstructor system configured to:

(a) create projection data arrays corresponding to the data obtained from each of the x-ray fan beams;

(b) apply a weighting function to each of the projection data arrays generated in step (a) to generate respective weighted projection data arrays, the weighting function to be applied for each data set, denoted as $W1(\beta,\gamma)$, $W2(\beta,\gamma)$, $W3(\beta,\gamma)$ and $W4(\beta,\gamma)$, being:

$$W1(\beta,\gamma) = 1/2 \begin{cases} 0 & \beta \leq \beta3_- \\ \frac{\beta - \beta3}{\beta1 - \beta3_-} & \beta3_- < \beta \leq \beta1 \\ \frac{\beta - \beta2}{\beta1 - \beta2} & \beta1 < \beta < \beta2_- \\ 0 & \beta \geq \beta2 \end{cases}$$

$$W2(\beta,\gamma) = \begin{cases} 0 & \beta \leq \beta3_- \\ w2_1(\beta,\gamma) + w2_2(\beta,\gamma) & \beta3_- < \beta \leq \beta2 \\ \frac{\beta - \beta3}{\beta2 - \beta3} & \beta2 < \beta < \beta3 \\ 0 & \beta \geq \beta3 \end{cases}$$

where:

$$w2_1(\beta,\gamma) = 1/2 \begin{cases} 0 & \beta \leq \beta1 \\ \frac{\beta - \beta1}{\beta2 - \beta1} & \beta1 < \beta \leq \beta2 \\ 0 & \beta \geq \beta2 \end{cases}$$

$$w2_2(\beta,\gamma) = 1/2 \begin{cases} 0 & \beta \leq \beta4_- \\ \frac{\beta - \beta4_-}{\beta2 - \beta4_-} & \beta4_- < \beta \leq \beta2 \\ 0 & \beta > \beta2 \end{cases}$$

$$W3(\beta,\gamma) = \begin{cases} 0 & \beta \leq \beta2 \\ \frac{\beta - \beta3}{\beta2 - \beta3} & \beta2 < \beta < \beta3 \\ w3_1(\beta,\gamma) + w3_2(\beta,\gamma) & \beta3 \leq \beta < \beta2_+ \\ 0 & \beta \geq \beta2_+ \end{cases}$$

where:

$$w3_1(\beta,\gamma) = 1/2 \begin{cases} 0 & \beta < \beta3 \\ \frac{\beta - \beta1_+}{\beta3 - \beta1_+} & \beta3 \leq \beta < \beta1_+ \\ 0 & \beta \geq \beta1_+ \end{cases}$$

$$w3_2(\beta,\gamma) = 1/2 \begin{cases} 0 & \beta < \beta3 \\ \frac{\beta - \beta4}{\beta3 - \beta4} & \beta3 \leq \beta < \beta4 \\ 0 & \beta \geq \beta4 \end{cases}$$

$$W4(\beta,\gamma) = 1/2 \begin{cases} 0 & \beta \leq \beta3 \\ \frac{\beta - \beta3}{\beta4 - \beta3} & \beta3 < \beta \leq \beta4 \\ \frac{\beta - \beta2_+}{\beta4 - \beta2_+} & \beta4 < \beta < \beta2_+ \\ 0 & \beta \geq \beta2_+ \end{cases}$$

(c) from the projection data arrays generated in step (b), generate image data arrays to be used to construct a slice image.

2. A system in accordance with claim 1 wherein generating image data arrays comprises the step of performing filtration and back projection on each weighted projection data array.

3. A system in accordance with claim 2 wherein prior to performing filtration and back projection, and the data arrays from a same gantry angle but from different detector rows are combined.

4. A system in accordance with claim 3 wherein if a projection view in a first data row are three hundred and sixty degrees from the a projection view in a fourth data row, combining the views prior to filtration and back projection.

5. A system in accordance with claim 1 wherein prior to applying a weighting function to each of the projection data arrays, storing the data in a system memory for reconstructing consecutive slices.

6. A system in accordance with claim 1 wherein said image reconstructor system is further configured to sum multiple thin slices within a desired slice profile if the desired slice profile is thicker than profiles supported by the data array.

7. A method for producing a tomographic image of an object from projection data acquired in a helical scan, said method comprising the steps of:

(a) creating projection data arrays corresponding to the data obtained from each of the x-ray fan beams;

(b) applying a weighting function to each of the projection data arrays generated in step (a) to generate respective weighted projection data arrays, the weighting factors to be applied for each data set, denoted as $W1(\beta,\gamma)$, $W2(\beta,\gamma)$, $W3(\beta,\gamma)$ and $W4(\beta,\gamma)$, being:

$$W1(\beta,\gamma) = 1/2 \begin{cases} 0 & \beta \leq \beta3_- \\ \frac{\beta - \beta3_-}{\beta1 - \beta3_-} & \beta3_- < \beta \leq \beta1 \\ \frac{\beta - \beta2}{\beta1 - \beta2} & \beta1 < \beta < \beta2_- \\ 0 & \beta \geq \beta2 \end{cases}$$

$$W2(\beta,\gamma) = \begin{cases} 0 & \beta \leq \beta3_- \\ w2_1(\beta,\gamma) + w2_2(\beta,\gamma) & \beta3_- < \beta \leq \beta2 \\ \frac{\beta - \beta3}{\beta2 - \beta3} & \beta2 < \beta < \beta3 \\ 0 & \beta \geq \beta3 \end{cases}$$

where:

$$w2_1(\beta,\gamma) = 1/2 \begin{cases} 0 & \beta \leq \beta1 \\ \frac{\beta - \beta1}{\beta2 - \beta1} & \beta1 < \beta \leq \beta2 \\ 0 & \beta \geq \beta2 \end{cases}$$

$$w2_2(\beta,\gamma) = 1/2 \begin{cases} 0 & \beta \leq \beta4_- \\ \frac{\beta - \beta4_-}{\beta2 - \beta4_-} & \beta4_- < \beta \leq \beta2 \\ 0 & \beta > \beta2 \end{cases}$$

$$W3(\beta,\gamma) = \begin{cases} 0 & \beta \leq \beta2 \\ \frac{\beta - \beta3}{\beta2 - \beta3} & \beta2 < \beta < \beta3 \\ w3_1(\beta,\gamma) + w3_2(\beta,\gamma) & \beta3 \leq \beta < \beta2_+ \\ 0 & \beta \geq \beta2_+ \end{cases}$$

where:

$$w3_1(\beta,\gamma) = 1/2 \begin{cases} 0 & \beta < \beta3 \\ \frac{\beta - \beta1_+}{\beta3 - \beta1_+} & \beta3 \leq \beta < \beta1_+ \\ 0 & \beta \geq \beta1_+ \end{cases}$$

$$w3_2(\beta,\gamma) = 1/2 \begin{cases} 0 & \beta < \beta3 \\ \frac{\beta - \beta4}{\beta3 - \beta4} & \beta3 \leq \beta < \beta4 \\ 0 & \beta \geq \beta4 \end{cases}$$

-continued $$W4(\beta,\gamma) = 1/2 \begin{cases} 0 & \beta \leq \beta3 \\ \frac{\beta - \beta3}{\beta4 - \beta3} & \beta3 < \beta \leq \beta4 \\ \frac{\beta - \beta2_+}{\beta4 - \beta2_+} & \beta4 < \beta < \beta2_+ \\ 0 & \beta \geq \beta2_+ \end{cases}$$

(c) from the projection data arrays generated in step (b), generating image data arrays to be used to construct a slice image.

8. A method in accordance with claim 7 wherein generating image data arrays comprises the step of performing filtration and back projection on each weighted projection data array.

9. A method in accordance with claim 8 wherein prior to performing filtration and back projection, and the data arrays from a same gantry angle but from different detector rows are combined.

10. A method in accordance with claim 9 wherein if a projection view in a first data row are three hundred and sixty degrees from the a projection view in a fourth data row, combining the views prior to performing filtration and back projection.

11. A method in accordance with claim 8 wherein prior to applying a weighting function to each of the projection data arrays, storing the data in a system memory for reconstructing consecutive slices.

12. A method in accordance with claim 8 wherein multiple thin slices within a desired slice profile are summed if the desired slice profile is thicker than profiles supported by the data array.

13. Apparatus for producing a tomographic image of an object from projection data acquired in a helical scan, said apparatus comprising:

(a) means for creating projection data arrays corresponding to the data obtained from each of the x-ray fan beams;

(b) means for applying a weighting function to each of the projection data arrays generated in step (a) to generate respective weighted projection data arrays, the weighting factors to be applied for each data set, denoted as $W1(\beta,\gamma)$, $W2(\beta,\gamma)$, $W3(\beta,\gamma)$ and $W4(\beta,\gamma)$, being:

$$W1(\beta,\gamma) = 1/2 \begin{cases} 0 & \beta \leq \beta3_- \\ \frac{\beta - \beta3}{\beta1 - \beta3_-} & \beta3_- < \beta \leq \beta1 \\ \frac{\beta - \beta2}{\beta1 - \beta2} & \beta1 < \beta < \beta2_- \\ 0 & \beta \geq \beta2 \end{cases}$$

$$W2(\beta,\gamma) = \begin{cases} 0 & \beta \leq \beta3_- \\ w2_1(\beta,\gamma) + w2_2(\beta,\gamma) & \beta3_- < \beta \leq \beta2 \\ \frac{\beta - \beta3}{\beta2 - \beta3} & \beta2 < \beta < \beta3 \\ 0 & \beta \geq \beta3 \end{cases}$$

where:

$$w2_1(\beta,\gamma) = 1/2 \begin{cases} 0 & \beta \leq \beta1 \\ \frac{\beta - \beta1}{\beta2 - \beta1} & \beta1 < \beta \leq \beta2 \\ 0 & \beta \geq \beta2 \end{cases}$$

$$w2_2(\beta, \gamma) = 1/2 \begin{cases} 0 & \beta \leq \beta4_- \\ \dfrac{\beta - \beta4_-}{\beta2 - \beta4_-} & \beta4_- < \beta \leq \beta2 \\ 0 & \beta > \beta2 \end{cases}$$

$$W3(\beta, \gamma) = \begin{cases} 0 & \beta \leq \beta2 \\ \dfrac{\beta - \beta3}{\beta2 - \beta3} & \beta2 < \beta < \beta3 \\ w3_1(\beta, \gamma) + w3_2(\beta, \gamma) & \beta3 \leq \beta < \beta2_+ \\ 0 & \beta \geq \beta2_+ \end{cases}$$

where:

$$w3_1(\beta, \gamma) = 1/2 \begin{cases} 0 & \beta < \beta3 \\ \dfrac{\beta - \beta1_+}{\beta3 - \beta1_+} & \beta3 \leq \beta < \beta1_+ \\ 0 & \beta \geq \beta1_+ \end{cases}$$

$$w3_2(\beta, \gamma) = 1/2 \begin{cases} 0 & \beta < \beta3 \\ \dfrac{\beta - \beta4}{\beta3 - \beta4} & \beta3 \leq \beta < \beta4 \\ 0 & \beta \geq \beta4 \end{cases}$$

$$W4(\beta, \gamma) = 1/2 \begin{cases} 0 & \beta \leq \beta3 \\ \dfrac{\beta - \beta3}{\beta4 - \beta3} & \beta3 < \beta \leq \beta4 \\ \dfrac{\beta - \beta2_+}{\beta4 - \beta2_+} & \beta4 < \beta < \beta2_+ \\ 0 & \beta \geq \beta2_+ \end{cases}$$

(c) means for constructing a slice image from the projection data arrays.

14. Apparatus in accordance with claim 13 wherein said means for generating image data arrays comprises means for performing filtration and back projection on each weighted projection data array.

15. Apparatus in accordance with claim 13 further comprising means for summing multiple thin slices within a desired slice profile.

* * * * *

UNITED STATES PATENT AND TRADEMARK OFFICE
CERTIFICATE OF CORRECTION

PATENT NO. : 5,541,970 Page 1 of 2
APPLICATION NO. : 08/436176
DATED : July 30, 1996
INVENTOR(S) : Hu It is certified that error appears in the above-identified patent and that said Letters Patent is hereby corrected as shown below:

In Specification, column 4, line 4, delete Equation (4) and insert therefor $$-- W1(\beta,\gamma) = 1/2 \begin{cases} 0 & \beta \leq \beta3_- \\ \dfrac{\beta - \beta3_-}{\beta1 - \beta3_-} & \beta3_- < \beta \leq \beta1 \\ \dfrac{\beta - \beta2_-}{\beta1 - \beta2} & \beta1 < \beta < \beta2_- \\ 0 & \beta \geq \beta2 \end{cases} --.$$

In Claim 1, column 6, beginning on line 1, delete the first equation and insert therefore $$-- W1(\beta,\gamma) = 1/2 \begin{cases} 0 & \beta \leq \beta3_- \\ \dfrac{\beta - \beta3_-}{\beta1 - \beta3_-} & \beta3_- < \beta \leq \beta1 \\ \dfrac{\beta - \beta2_-}{\beta1 - \beta2} & \beta1 < \beta < \beta2_- \\ 0 & \beta \geq \beta2 \end{cases} --.$$

UNITED STATES PATENT AND TRADEMARK OFFICE
CERTIFICATE OF CORRECTION

PATENT NO. : 5,541,970
APPLICATION NO. : 08/436176
DATED : July 30, 1996
INVENTOR(S) : Hu It is certified that error appears in the above-identified patent and that said Letters Patent is hereby corrected as shown below:

In Claim 7, column 7, beginning on line 22, delete the first equation and insert therefore $$-- W1(\beta,\gamma) = 1/2 \begin{cases} 0 & \beta \leq \beta3_- \\ \dfrac{\beta - \beta3_-}{\beta1 - \beta3_-} & \beta3_- < \beta \leq \beta1 \\ \dfrac{\beta - \beta2_-}{\beta1 - \beta2} & \beta1 < \beta < \beta2_- \\ 0 & \beta \geq \beta2 \end{cases} --.$$

In Claim 13, column 8, beginning on line 46, delete the first equation and insert therefore $$-- W1(\beta,\gamma) = 1/2 \begin{cases} 0 & \beta \leq \beta3_- \\ \dfrac{\beta - \beta3_-}{\beta1 - \beta3_-} & \beta3_- < \beta \leq \beta1 \\ \dfrac{\beta - \beta2_-}{\beta1 - \beta2} & \beta1 < \beta < \beta2_- \\ 0 & \beta \geq \beta2 \end{cases} --.$$

Signed and Sealed this

Twenty-eighth Day of November, 2006

JON W. DUDAS
*Director of the United States Patent and Trademark Office*